United States Patent [19]

Sanders

[11] Patent Number: 4,815,464
[45] Date of Patent: * Mar. 28, 1989

[54] METHODS FOR TEMPOROMANDIBULAR JOINT SMALL INCISION SURGERY

[76] Inventor: Bruce Sanders, 3629 Seahorn Dr., Malibu, Calif. 90265

[*] Notice: The portion of the term of this patent subsequent to Mar. 24, 2004 has been disclaimed.

[21] Appl. No.: 29,071

[22] Filed: Mar. 23, 1987

Related U.S. Application Data

[63] Continuation-in-part of Ser. No. 825,334, Feb. 1, 1986, Pat. No. 4,651,736.

[51] Int. Cl.⁴ .............................................. A61B 17/32
[52] U.S. Cl. .................................................... 128/305
[58] Field of Search .................... 128/305, 751, 305.1, 128/303 R, 752–755; 604/22

[56] References Cited

U.S. PATENT DOCUMENTS

| | | | |
|---|---|---|---|
| 4,203,444 | 5/1980 | Bonnell et al. | 128/305 |
| 4,499,899 | 2/1985 | Lyons | 128/6 |

FOREIGN PATENT DOCUMENTS

| | | | |
|---|---|---|---|
| 3007165 | 9/1981 | Fed. Rep. of Germany | 128/305 |
| 2093353 | 9/1982 | United Kingdom | 128/305 |

Primary Examiner—Michael H. Thaler

[57] ABSTRACT

The present invention provides improved methods for correction of temporomandibular joint internal derangement with closed lock via small incision surgical technique. In one embodied form, the unique method comprises the steps of: (a) effecting visualization and orientation of the surgical site of a patient utilizing an arthroscopic device comprising a mechanism for prescribed calibration of the arthroscope depth; (b) effecting arthroscopic inspection of the surgical site, and in particular, the superior compartment of the temporomandibular joint; and (c) effecting lysis comprising resection and incision of adhesions disposed between disc and fossa of the temporomandibular joint region, concommittent with disc displacement. The inventive surgical technique includes an "arthroscopic sweep" of the superior compartment of the TMJ with lysis comprising resects of superior compartment adhesions. Subsequent to lysis, the superior compartment is thoroughly lavaged via irrigation and suction. Preferably, a pressure dressing is placed to cover the surgical wound, and can be removed within about 12 hours from the surgical procedure.

10 Claims, 5 Drawing Sheets

ARTHROSCOPIC SWEEP:
LYSIS OF ADHESIONS

INFERIOR COMPARTMENT
POSTERIOR RECESS

CONDYLE          POSTERIOR
                 ATTACHMENT

ARTHROSCOPIC SWEEP:
LYSIS OF ADHESIONS

Fig. 9a. Two relatively small wounds for TMJ small incision surgery.

Fig. 9b. Illustrating full mandibular opening and excursive movement, one to four days after surgery.

METHODS FOR TEMPOROMANDIBULAR JOINT SMALL INCISION SURGERY

This application is a continuation-in-part of application Ser. No. 825,334, filed Feb. 1, 1986 now U.S. Pat. No. 4,651,736.

BACKGROUND OF THE INVENTION

This invention relates to arthroscopic surgery of the temporomandibular joint (TMJ) and methods and devices for incision, excision, repositioning, recontouring, and replacement of joint fluids and soft and hard tissues by "less invasive surgery" technique.

The temporomandibular joint (TMJ) is the freely movable articulation between the condyle of the mandible and the squamous portion of the temporal bone. While having much in common with other synovial joints of the body, there are several anatomic and functional characteristics that distinguish the TMJ from most other synovial joints. These distinctions are as follows:

(a) The articulating surfaces of the bones are covered by an avascular fibrous connective tissue that may contain a variable number of cartilage cells and thus can be designated fibrocartilage.

(b) The two articulating complexes of bone carry teeth, whose shape and position influence the movements of the joint. It is the only joint with a rigid endpoint of closure.

(c) It has a bilateral articulation with the cranium, so the right and left temporomandibular articulations must function together.

(d) The TMJ is a complex joint because each joint has an articular disc (meniscus) interposed between the condyle and the temporal bone.

The TMJ is a combined hinge-glide articulation of the mandibular condyle with the mandibular fossa and articular eminence of the temporal bone. The muscles of mastication and the suprahyoid muscles act bilaterally to produce three types fo movement: rotation, translation, and a combination of rotation and translation movement of the condyles. Rotation and some slight translation take place in the lower joint space between the condyle and the articular disc. Translation of the condyle-disc complex takes place in the upper joint space.

Changes in the disc-condyle relationship often produces pain and/or functional disturbances in the masticatory system. The disc is most commonly displaced anteromedially and, in the last few years, the term "internal derangements of the TMJ" connotes any disturbance between the articulating components within the joint proper.

Little is known about the prevalence of displacement. Some authors (W. L. McCarty, Jr. and W. Farrar: Surgery for Internal Derangements of the Temporomandibular Joint. J. Prosthet Dent 42:2 79) maintain that it is extremely common, whereas others believe it is rare. In a recent autopsy study of young adults, (W. Solberg, T. Hanson, B. Nordstrom: Morphologic Evaluation of Young Adult TMJs at Autopsy, abstracted J. Dent Res 63:228 1984), found disc displacement in 11.6% of the TMJs and noted it to be present more commonly in women. In other study of adult cadavers by PL. Westesson and M. Rohlin, Internal Derangement Related to Osteoarthrosis in Temporomandibular Joint Autopsy Specimens, Oral Surg 57:17, 1984, disc placement was found in 56% of the TMJs. Thus, the prevalance of disc displacement appears to increase with age.

Persistent (chronic) "closed locking" of the temporomandibular joint has been attributed to internal derangement due to anterior disc displacement without reduction. Anatomic, arthrographic, clinical, and surgical studies have supported this concept. Among such studies is C. H. Wilkes: Structural and Functional Alterations of the Temporomandibular Joint. Northwest Dent 57:287, 1978 and C. H. Wilkes: Arthrography of the Temporomandibular Joint in Patients With the TMJ Pain-Dysfunction Syndrome. Minn Med 61:645, 1978.

The natural history of internal derangement leading to persistent "closed lock" has been described by V. E. Ireland: The problem of "The Clicking Jaw". Proc. R. Soc. Med. 44:191, 1951 and M. F. Dolwick, R. W. Katzberg, C. A. Helms: Internal Derangement of the Temporomandibular Joint: Fact or Fiction? J Prosthet Dent 49:415, 1983. Trauma to the mandible has been reported to be a common etiologic factor leading to the development of internal derangement with closed lock. The traumatic event may result not only in disc displacement, but also intracapsular microbleeding and effusion. Subsequent adhesions may form. These adhesions are most commonly seen in the superior compartment. Additionally, morphological changes occur in the TMJ including synovitis and synovial hyperplasia.

Treatment of acute closed locking of the TMJ may include mandibular manipulation, splint therapy, and other non-surgical therapy. These modalities are intended to "recapture" the displaced disc. If "non-invasive therapy" is not successful, a persistent (chronic) closed lock may occur.

A plethora of evidence exists demonstrating the reality of disc displacement. This evidence includes clinical, anatomic, radiographic, and surgical findings. It has been shown that the TMJ disc is displaced anteromedially and that the displaced disc can mechanically interfere with jaw movement.

P. L. Westesson and M. Rohlin: Internal Derangement Related to Osteoarthrosis in Temporomandibular Joint Autopsy Specimens, Oral Surg 57:17, 1984, studying adult cadaver TMJs, have shown a progression of internal derangements that includes not only changes in disc position but also in disc configuration. A progression from oblique disc position with biconcave disc or disc of even thickness to complete displacement with biconvex disc configuration was shown. The most advanced form of internal derangement showed perforation of the disc and/or its attachment tissues. The occurrence of osteoarthrosis was observed to increase with more advanced disc displacement and changes in disc configuration. Discs of even thickness were associated with osteoarthrosis in 50% compared to 90% for biconvex discs.

The disclosures of the foregoing references are hereby incorporated by this reference.

Temporomandibular joint surgery via arthrotomy (open surgical approach) has been widely advocated for treatment of internal derangements with closed lock when non-surgical therapy has failed. Preauricular, endaural, and postauricular approaches have been employed by various clinicians. Disc repositioning, arthroplasty, meniscectomy with implant, and other procedures have been described to treat internal derangement.

However, one of the principal disadvantages of open surgical approach is that a relatively large incision is necessary to perform two basic procedures: disc repositioning and disc removal. Typically, a curvalinear incision of 6 to 7 centimeters is made and extended through skin and subcutaneous tissues to the depth of the temporalis fascia. The superior part of the flap is extended anteriorly by blunt dissection with a periosteal elevator. The flap is developed inferiorally adjacent to the external auditary cartilage. Usually, a vein crosses the lateral aspect of the articular fossa. This vein while identifying the correct depth of the capsule, is generally dissected out, clamped, divided, and ligated or cauterized.

An oblique incision, parallel to the temporal branches of the facial nerve, is typically made through the superficial layer of the temporal fascia. The incision may extend to bone over the lateral part of the fossa. Its inferior aspect generally should be no farther than 8 millimeters in front of the tragus of the ear. As before, the lateral aspect of the fossa is exposed by blunt dissection with a periosteal elevator.

This type of surgical procedure can lead to a relatively high complication rate, among other disadvantages. For instance, the serious dangers associated with TMJ surgery via arthrotomy include facial nerve paralysis with inability to close eyelid on the affected side, and inability to wrinkle the forehead, post-operative infection, resultant malocclusion (incorrect bite) and limited opening, lack of improvement or worsening of pain and jaw dysfunction; and further degenerative changes with the TMJ.

Accordingly, those skilled in the art have recognized a significant need for TMJ arthroscopic surgical treatment which affords the clinical advantages of using relatively small incision techniques, yet possesses the requirements thereby providing a safer and more convenient surgical procedure and more comfortable therapy for the patient.

SUMMARY OF THE INVENTION

The disclosed "less invasive surgery" methodology is an alternative approach to conventional surgical correction of TMJ internal derangement with closed lock.

In one embodied form, the unique methodology comprises the steps of:

(a) effecting visualization and orientation of the surgical site of a patient by utilizing an arthroscopic device comprising means for prescribed calibration of arthroscope depth;

(b) effecting arthroscopic inspection of the surgical site and, in particular, the superior compartment of the temporomandibular joint; and (c) effecting lysis comprising resection and incision of adhesions disposed between disc and fossa of the temporomandibular joint region, concommittent with disc displacement.

The inventive surgical technique includes an "arthroscopic sweep" of the superior compartment of the TMJ with lysis comprising resects of superior compartment adhesions. Subsequent to the lysis, the superior compartment is thoroughly lavaged via irrigation and suction. Preferably, a pressure dressing is placed to cover the surgical wound, and can be removed within about 12 hours from the surgical procedure.

Excision or recontouring of relatively soft and hard tissues in the temporomandibular joint area can be effected with mini-shaver devices and/or surgical grinders. Repositioning of a displaced disc may be effected by a variety of techniques, including manipulation, scarification and thermal or photocoagulation of the posterior attachment of the disc. In this respect, synovial fluid may be replaced by biocompatible solutions including medicaments.

In accordance with the present invention, the relatively small surgical wounds heal rapidly and full mandibular opening and excursive movements by a patient undergoing the surgical procedure are typically present within one to four days after surgery.

Optionally, a stabilizing (non-repositioning) bite splint may be employed to assist patient healing postoperatively.

Accordingly, the present invention provides arthroscopic surgery to correct persistent closed locking of the temporomandibular joint which is a preferred alternative to arthrotomy.

Where replacement of the TMJ is required, the present invention provides deformable TMJ implant structures having prescribed memory characteristics which enable the TMJ implant to be deformed by compressing, rolling, folding, stretching, or by a combination thereof, to a diameter of 80% or less of the cross-sectional diameter of the TMJ implant, yet return to its original configuration, full size and fixed focal length after insertion through the relatively small incision. The unique deformable implants can be fabricated from selected biologically inert materials possessing superior elasticity and compression characteristics and optionally, may include a wide variety of fixating means for placement of the implant and to maintain its contour within the capsule.

The above and other objects and advantages will become apparent from the following more detailed description of the invention, taken in conjunction with the drawings.

DESCRIPTION OF THE PREFERRED EMBODIMENTS

Arthroscopy is performed in the operating room under general anesthesia with nasoendotracheal intubation. Typically, all procedures being with arthroscopic examination. Definitive treatment with arthroscopic surgery or arthrotomy is determined by arthroscopic findings.

The arthroscopic technique generally begins with an assistant surgeon manipulating the mandibular condyle anteriorly and inferiorly.

Several anatomic structures in the preauricular region are important when performing TMJ surgery.

Figure 1:
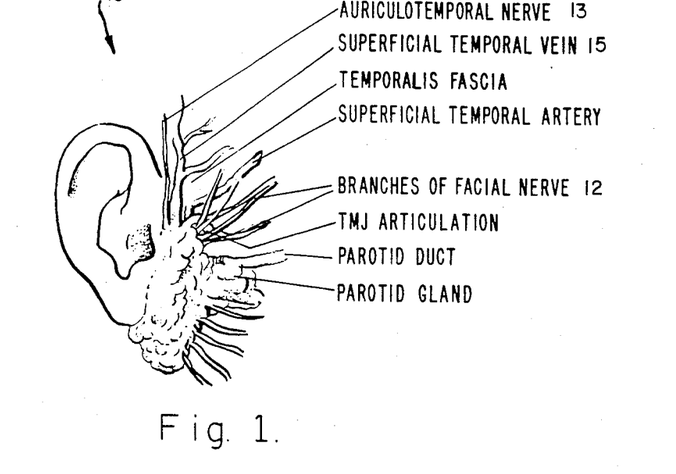
FIG. 1 is a schematic illustration of a preauricular region of a patient.

Referring to FIG. 1, there is shown an illustration of the preauricular region, generally denoted 10, includes the parotid gland 11, superficial temporal vessels, and facial and auriculotemporal nerves 12 and 13.

The parotid gland lies below the zygomatic arch, below and in front of the external acoustic meatus, on the masseter muscle, and behind the ramus of the mandible. The superior pole of the parotid gland lies over the TMJ. The parotid gland is enclosed within a capsule derived from the investing layer of the deep cervical fascia.

The superficial temporal vessels emerge from the superior aspect of the gland and accompany the auriculotemporal nerve 14. The superficial temporal artery arises in the parotid gland 11, crosses the zygomatic arch, and divides into frontal and parietal branches. The superficial temporal vein 15 lies superficial to the artery. The auriculotemporal nerve 13 accompanies, and is posterior to, the superficial temporal artery. The terminal branches of the facial nerve emerge from the parotid gland 11 and radiate forward in the face. The terminal branches vary in their arrangement but are commonly classified as temporal, zygomatic, buccal, marginal mandibular, and cervical. The location of the temporal branches is of particular importance during TMJ surgery, as these are the branches most likely to be encountered in the surgical field. The termporal nerve branches lie within a dense fusion of periosteum, temporal fascia, and superficial fascia at the leval of the zygomatic arch.

Figure 2:
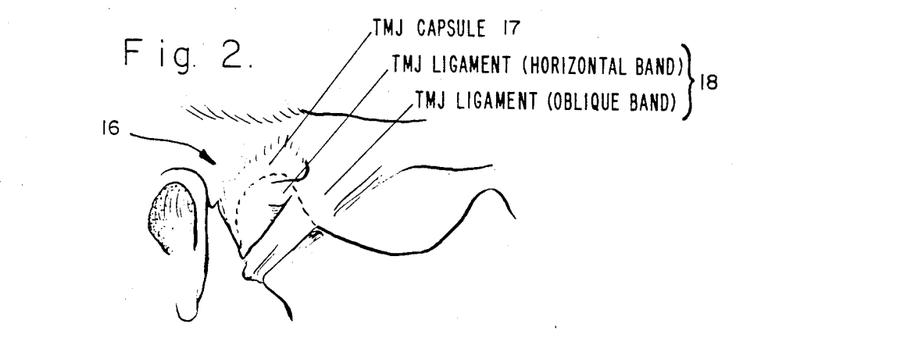
FIG. 2 is a schematic illustration of a temporomandibular joint of a patient.

The TMJ 16, as shown in FIG. 2, is an encapsulated articulation. The capsule 17 defines the anatomic and functional boundaries of the TMJ 16. The thin, loose fibrous capsule surrounds the articular surface of the condyle and blends with the periosteum of the mandibular neck.

The articular capsule 17 is strongly reinforced laterally by the temporomandibular (lateral) ligament 18, which is composed of a superficial fan-shaped layer of obliquely oriented connective tissue fibers and a deeper, narrow band of fibers that run more horizontally. The ligament attaches broadly to the outer surface of the root of the zygomatic arch and coverges downward and backward to attach to the back of the condyle below and behind its lateral pole.

The principal biomechanical function of the temporomandibular ligament, acting singly or with its controlateral mate, is to "check" or limit movements of the condyle-disc complex. It is by far the most important ligament associated with the TMJ. A primary function of this ligament is to limit retrusion of the condyle against retrocondylar structures, for example, posterior disc attachment tissues. This ligament prevents the condyle disc complex from being displaced away from the articular eminence and limits the anterior movement of the condyle.

Figure 3:
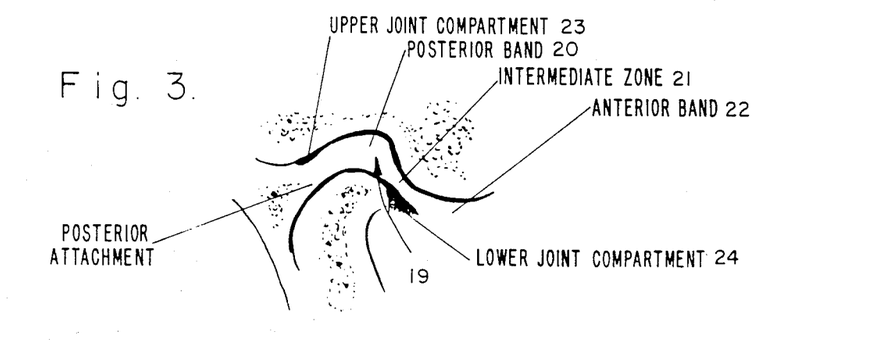
FIG. 3 is a schematic illustration of an articular disc.

Referring now to FIG. 3, there is shown in schematic form, an articular disc 19 of a firm but flexible structure with a specialized shape and function. The disc is illustrated and divided into three regions: posterior band 20, intermediate zone 21, and anterior band 22. The central zone is considerably thinner (1 millimeter) than the posterior and anterior bands. The posterior band is generally thicker (3 millimeters) than the anterior band (2 millimeters). The upper surface of the disc adapts to the contours of the fossa and eminence of the temporal bone, and the lower surface of the disc adapts to the contour of the mandibular condyle.

Posteriorly the disc is contiguous with the loosely organized posterior attachment tissues (bilaminar zone, retrodiscal pad). The posterior attachment tissues are attached to the tympanic plate of the temporal bone posterosuperiorly and to the neck of the condyle posteroinferiorly.

Anteriorly the disc is contiguous with the capsule and the fascia of the superior head of the lateral pterygoid muscle. The superior head of the lateral pterygoid muscle may have some fibers inserting directly into the disc anteromedially.

The disc 19 and its attachments illustrated in FIG. 3 divide the joint space into separate superior and inferior spaces. In the sagittal plane the upper joint space is contiguous with the glenoid fossa and the articular eminence. It generally extends to the greatest curvature of the articular eminence. The upper joint space 23 always extends farther anteriorly than the lower joint space 24. The lower joint 24 is contiguous with the condyle and extends only slightly anterior to the condyle along the superior aspect of the superior head of the lateral pterygoid muscle.

The inventive procedures provide an alternative approach to the conventional surgical correction of temporomandibular joint internal derangement with closed lock via arthrotomy (open surgical approach). The unique methodology includes arthroscopic inspection of the superior compartment and lysis (resection, ablation) of adhesions that form between the disc and fossa concommitant with disc displacement. These disc-fossa surface adhesions prevent relocation of the displaced disc by non-surgical methods. The disc is immobile due to the superior compartment adhesions. By using an elevator during the arthrotomy procedure the adhesions can be released, and the disc may appear to move normally again.

Figure 4:
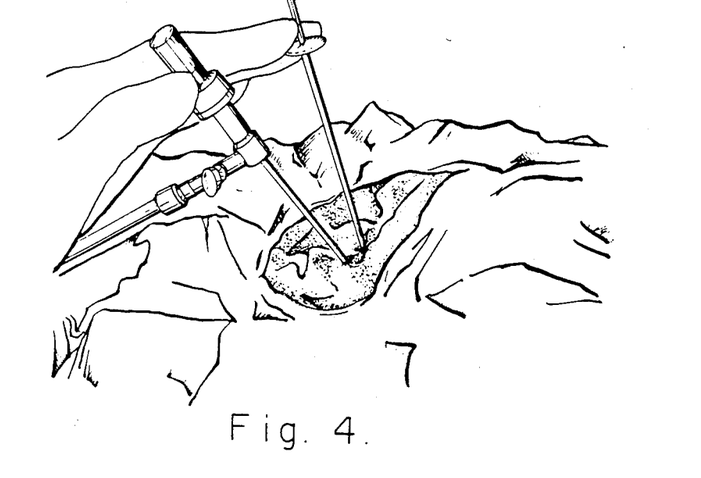
FIG. 4 depicts the establishment of an inflow mechanism and a separate outflow mechanism via a separate anterior portal.

In one embodied form, the arthroscopic technique begins with the assistant surgeon manipulating the mandibular condyle anteriorly and inferiorly. The superior compartment was entered with a twenty-gauge needle and one to two millimeters of ½% xylocaine with 1:200,000 epinephrine was injected. Next, three to four millimeters of normal saline was injected. Using a R. Wolf 1.9 mini-arthroscopic sharp trochar in a sheath, the superior compartment was entered. The blunt trochar replaced the sharp trochar and a minimal sweeping action created space between the disc and the fossa. The inflow mechanism was established, and a separate outflow mechanism was created via a separate anterior portal (FIG. 4). The 1.9 millimeter R. Wolf arthroscope replaced the blunt trochar in the sheath. A tube camera and light source are attached and the arthroscopic examination was visualized on the television monitor and is recorded on video tape or other suitable media.

Arthroscopic examination of the superior compartment was commenced in the posterior recess. The posterior attachment and posterior fossa wall are visualized. Next the descending aspect of central portion of the disc was examined. Then the ascending portion of central portion of the disc was visualized. Finally the anterior recess, articular eminence, and anterior portion of the disc was visualized.

Figure 5:
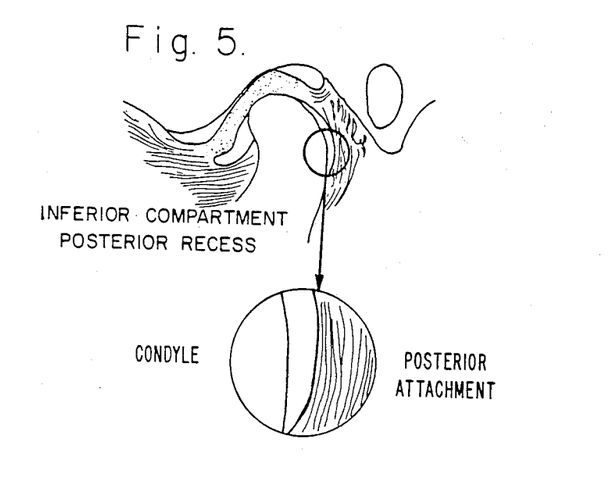
FIG. 5 is an illustration of adhesions most commonly seen in the superior compartment forming surface adhesions from the disc to the fossa.

Detailed intracapsular pathology can be documented by the foregoing procedure. Synovial adhesions in the superior compartment appear to be the primary reason why a displaced disc does not reduce and why a closed lock persists. These adhesions are most commonly seen in the superior compartment forming surface adhesions from the disc to the fossa, especially anteriorly between the posterior slope of the eminence and the central portion of the disc (FIG. 5). Masses of synovial tissue can be seen in patients with chronic inflammation. Changes in the vascularity of the posterior attachment are easily seen. A hypermia of the posterior attachment and synovial lining is observed in many closed lock cases. Changes in the position mobility, contour, coloration, and thickness of the disc can be observed. Perforations of the disc and posterior attachment can be visualized.

Figure 6:
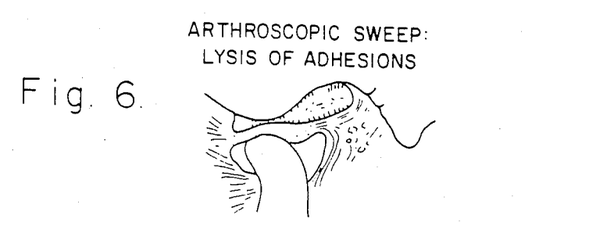
FIG. 6 depicts an "arthroscopic sweep" of the superior compartment which lyses (resects) the superior compartment adhesions.
Figure 7:
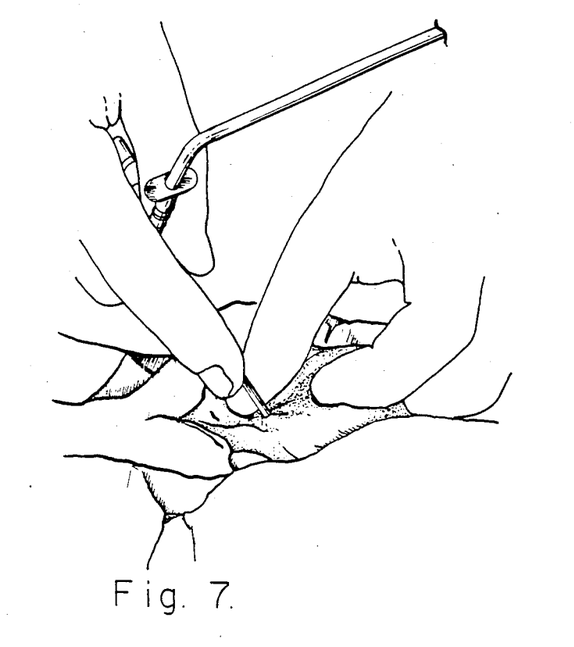
FIG. 7 illustrates the arthroscopic sweep effected with a blunt trochar.
Figure 8:
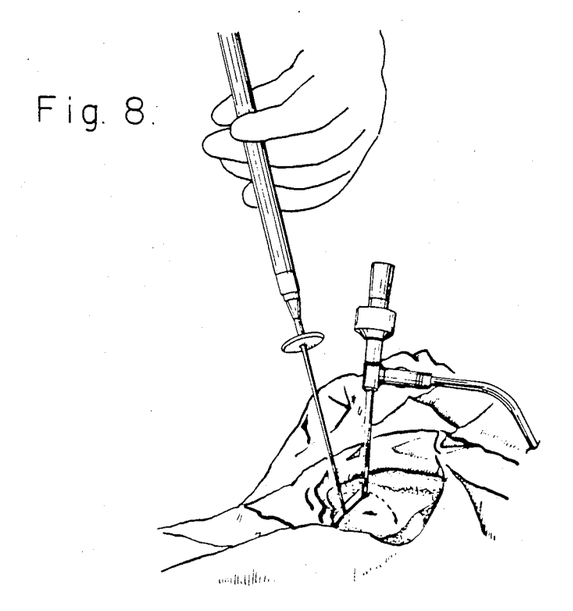
FIG. 8 illustrates lavage of the superior compartment via irrigation and suction.
Figure 9A:
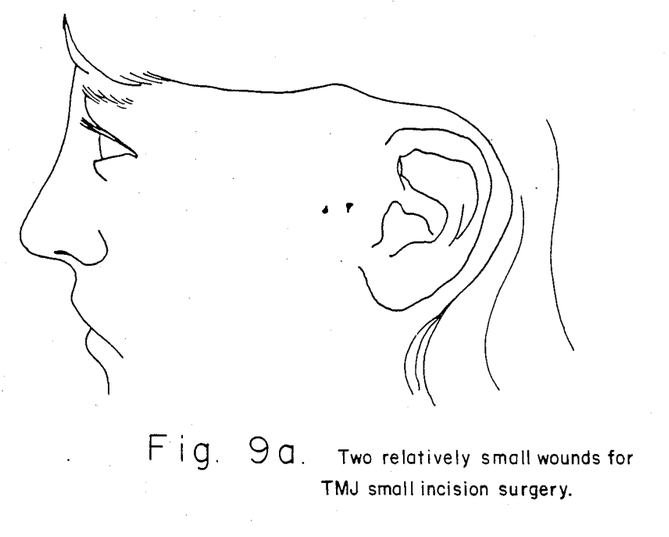
FIG. 9 illustrates full mandibular opening and excursive movements of a patient within one to four days after surgery.
Figure 9B:
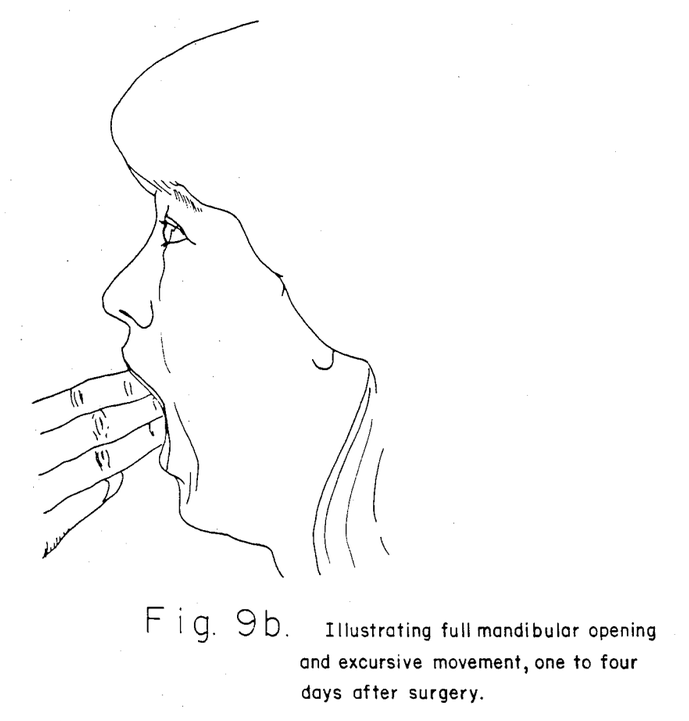

Arthroscopic surgery is a highly effective method for releasing a persistent (chronic) closed lock. Surgical technique consists of an "arthroscopic sweep" of the superior compartment which lyses (resects) the superior compartment adhesions (FIG. 6). This maneuver is done with the blunt trochar (FIG. 7). The temporomandibular joint immediately becomes mobile and condylar translation becomes possible. The superior compartment is thoroughly lavaged via irrigation and suction (FIG. 8). A small amount of steroid solution is placed in the superior compartment when the tissues appear inflammed. There is usually no need for any sutures. A pressure dressing is placed, but is removed that evening. The patient is usually discharged the next day. The wounds heal rapidly. Full mandibular opening and excursive movements are present within one to four days (FIG. 9). A stabilizing (non-repositioning) bite splint is employed post-operatively.

Figure 10:
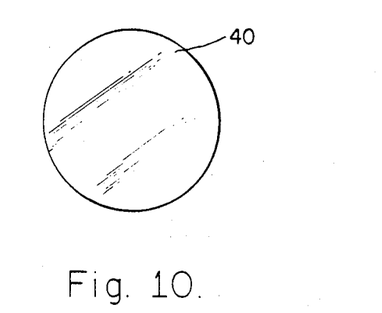
FIG. 10 is an illustration of a deformable TMJ implant in accordance with the present invention which is suitable for replacement of an excised articulate disc.

FIG. 10 depicts a deformable TMJ implant 40 in accordance with the present invention which is suitable for replacement of an excised articulate disc. In the embodied form shown, there are no fixation appendages and the implantation comprises a deformable elliptic portion imparted with desirable memory characteristics, appropriate structural dimensions, and composed of a deformable material such that the implant can be deformed to an appropriate size for insertion into the fossa.

Typically, the elliptic portion of the implantation is composed of one or more materials selected from the group consisting of silastic sheeting, teflon, polyurethane elastomer, silicone elastomer, hydrogel plastic, collagen, organic or synthetic gels or combinations thereof. In one embodied form, the elliptic portion of the implant can be fabricated from one of the foregoing materials, and further comprise a thin surface layer or layers of a second or third material.

The inventive implant can be fabricated having a wide variety of cross-sections designed for replacement of the surgically removed human articular disc. In this respect, the implant may have a convex; plano convex; a plano concave; a biconcave; or a concave-convex cross-section.

Figure 11:
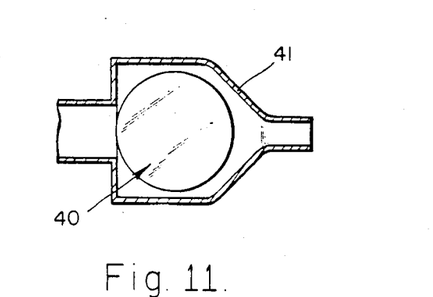
FIG. 11 depicts an implant holding compartment of a surgical device for implantation of deformable TMJ implants.
Figure 12:
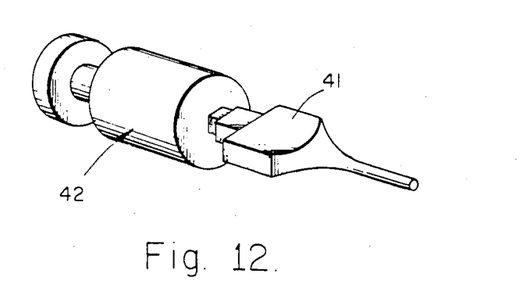
FIG. 12 is a further illustration of one embodied form of a surgical device for implantation of deformable TMJ implants.

FIG. 11 most clearly illustrates the implant holding compartment 41 of the device 42 shown in FIG. 12 having an implant holding compartment composed of transparent material and appropriately designed to contain the implant in a natural, unstressed state. Preferably, the implant before insertion and within the compartment, is suspended in a liquid medium such as distilled water, saline or a biocompatible lubricating fluid such as hyaluronic acid or condroit in sulfate. In the figure shown, the compartment is adapted to hold an implant without supporting appendages and having an elliptic portion. However, it should be understood that such compartment can be adapted in configuration to facilitate placement of various implants in accordance with the present invention.

Preferably, visualization and orientation of the surgical site is effected by utilizing an arthroscopic device comprising means for prescribed calibration of the arthroscope depth. As insertion of the device into the wound must be carefully controlled to avoid penetration into delicate surrounding tissue, an inventive arthroscope has been developed comprising adjustable means along the outer sleeve of the arthroscope to assist the surgeon in proper insertion of the tool. One particularly suitable calibration means for the inventive device comprises a resilient girdle movable on the shaft of the arthroscope.

In accordance with the present invention, improved methods are provided for correction of temporomandibular joint internal derangement with closed lock via small incision surgical technique. These methods comprise the steps of:

(a) manipulating the mandibular condyle of a patient anteriorially and inferiorially;

(b) entering the superior compartment of the patient's temporomandibular joint with a surgical needle and injecting therein a solution comprising anesthetic;

(c) injecting into said superior compartment saline solution;

(d) entering the superior compartment with an arthroscopic device for visualization of the internal condition of the temporomandibular joint;

(e) determining whether synovial adhesions are present in the superior compartment of the temporomandibular joint; and (f) effecting lyses comprising resection and incision of adhesions disposed between disc and fossa of the temporomandibular joint region, concommittent with disc displacement.

The improved methods for correction may further comprise the step of effecting arthroscopic sweep of the superior compartment of the temporomandibular joint.

Arthroscopy of the temporomandibular joint has proven to be a highly effective small incision surgery technique as described above.

As stated previously, arthroscopic sweep of the superior compartment can lyse adhesions that cause closed locking of the mandible. Additionally, in earlier cases in younger patients, there are situations in closed locking where there are no adhesions. However, there is a phenomenon I have termed "suction-cup effect" where the disc is stuck via surface tension to the articular eminence and fossa without interpositional adhesions. Small incision surgery with TMJ arthroscopy can "decompress" and eliminate the "suction-cup effect" via sweep, joint lavage, and manipulation of the mandible.

Conversely, in cases of very advanced osteoarthritis of the TMJ (degenerative joint disease) or rheumatoid arthritis where the articular disc is quite degenerative, deformed, or perforated, small incision surgery with arthroscopic techniques can be efficacious. Lysis of adhesions, joint lavage, and removal of diseased tissue are treatments of choice.

Joint lavage with specialized therapeutic solutions including anti-inflammatory and/or anti-biotic medicaments is helpful in eliminating hyperemia and debris from the TMJ.

Preferably, the active anti-inflammatory medicament is ultra-pure hyaluronic acid. In joints and bursae, the hyaluronic acid can be used to impede the development of intra articular fibrosis tissue (pannus, ankylosis, adhesions) and to support the healing process of cartilege and synovial tissue. Those skilled in the art will readily appreciate the wide variety of hyaluronic acid compositions useful in accordance with the present invention and further disclosure may be had by reference to U.S. Pat. No. 4,141,973, issued to Endre Balazs on Feb. 27, 1979, which disclosure is hereby incorporated by this reference.

The preferred antibiotic is a broad spectrum antibiotic, for instance penicillin compound.

"Cutting" hand instruments and grasping forceps and power rotary devices that can be placed into the TMJ via small incision surgery can be utilized to excise diseased tissue and recontour articular surfaces within the joint.

The described surgical technqiues in accordance with the present invention, thus minimize the principal disadvantages attendant with conventional TMJ surgery via arthrotomy which requires a relatively large incision in the tissue among other disadvantages, leads to a relatively high complication rate.

It will be apparent from the foregoing that while particular forms of the invention have been illustrated and described, various modifications can be made without department from the spirit and scope of the invention. Accordingly, it is not intended that the invention be limited except as by the appended claims.

I claim:

1. An improved method for correction of temporomandibular joint internal derangement with closed lock via small incision surgical technique, said joint comprising a mandibular condyle, superior compartment having, posterior attachment and posterior fossa, the method comprising the steps of:
   (a) manipulating said mandibular condyle of a patient anteriorially and inferiorially;
   (b) entering the superior compartment of the patient's temporomandibular joint with a surgical needle and injecting therein a solution comprising anesthetic;
   (c) injecting into said superior compartment saline solution;
   (d) entering said superior compartment with an arthroscopic device for visualization of the internal condition of the temporomandibular joint;
   (e) determining whether synovial adhesions are present in said superior compartment of the temporomandibular joint;
   (f) effecting lyses comprising resection and incision of adhesions disposed between disc and fossa of the temporomandibular joint region, concommittent with disc displacement; and
   (g) effecting joint lavage with therapeutic solution comprising an efficacious amount of anti-inflammatory medicament to impede the development of intra articular fibrosis tissue and to support the healing process of cartilage and synovial tissue.

2. The improved method for correction of temporomandibular joint internal derangement with closed lock as defined in claim 1 wherein said step of effecting visualization comprises effecting arthroscopic examination of said superior compartment commencing in the posterior recess.

3. The improved method for correction of temporomandibular joint internal derangement with closed lock as defined in claim 1 wherein said step of effecting visualization comprises visualizing the posterior attachment and posterior fossa all of the patient.

4. The improved method for correction of temporomandibular joint internal derangement with closed lock as defined in claim 1 wherein said step of effecting visualization comprises examining the descending aspect of the central portion of the disc.

5. The improved method for correction of temporomandibular joint internal derangement with closed lock as defined in claim 1 wherein said step of effecting visualization comprises examining the ascending portion of the central portion of the disc.

6. The improved method for correction of temporomandibular joint internal derangement with closed lock as defined in claim 1 wherein said step of effecting visualization comprises effecting visualization of the anterior recess, articular eminence and anterior portion of the disc.

7. An improved method for correction of temporomandibular joint internal derangement with closed lock via small incision surgical technique, said joint comprising a mandibular condyle, superior compartment having, posterior attachment and posterior fossa, the method comprising the steps of:
   (a) manipulating said mandibular condyle of a patient anteriorially and inferiorially;
   (b) entering the superior compartment of the patient's temporomandibular joint with a surgical needle and injecting therein a solution comprising anesthetic;
   (c) injecting into said superior compartment saline solution;
   (d) entering said superior compartment with an arthroscopic device for visualization of the internal condition of the temporomandibular joint;
   (e) determining whether synovial adhesions are present in said superior compartment of the temporomandibular joint;
   (f) effecting lyses comprising resection and incision of adhesions disposed between disc and fossa of the temporomandibular joint region, concommittent with disc displacement; and
   (g) effecting joint lavage with therapeutic solution comprising an efficacious amount of broad spectrum antibiotic medicament to help eliminate hyperemia and debris from the temporomandibular joint.

8. The improved method for correction of temporomandibular joint internal derangement with closed lock as defined in claim 7 and further comprising the step of thoroughly lavaging the superior compartment via irrigation of saline solution and aspiration of said solution.

9. The improved method for correction of temporomandibular joint internal derangement with closed lock as defined in claim 8 and further comprising the step of introducing into said lavaged area steroid solution in said superior compartment.

10. The improved method for correction of temporomandibular joint internal derangment with closed lock as defined in claim 9 and further comprising the step of placing a pressure surgical dressing on the surgical site.

* * * * *